(12) United States Patent
Kolich

(10) Patent No.: US 8,448,739 B2
(45) Date of Patent: May 28, 2013

(54) IN-VEHICLE SMELL NOTIFICATION SYSTEM

(75) Inventor: Michael Kolich, Windsor (CA)

(73) Assignee: Ford Global Technologies, LLC, Dearborn, MI (US)

( * ) Notice: Subject to any disclaimer, the term of this patent is extended or adjusted under 35 U.S.C. 154(b) by 836 days.

(21) Appl. No.: 12/582,320

(22) Filed: Oct. 20, 2009

(65) Prior Publication Data

US 2011/0089255 A1 Apr. 21, 2011

(51) Int. Cl.
*B60R 21/00* (2006.01)
*B60R 21/013* (2006.01)

(52) U.S. Cl.
USPC .......................................... 180/271; 180/272

(58) Field of Classification Search
USPC ............ 180/271, 272; 261/DIG. 17, DIG. 18, 261/DIG. 89; 422/120, 124; 454/152, 157
See application file for complete search history.

(56) References Cited

U.S. PATENT DOCUMENTS

| | | | |
|---|---|---|---|
| 3,259,050 A * | 7/1966 | Grimm, III | 454/157 |
| 4,309,382 A * | 1/1982 | Miller | 422/4 |
| 4,629,604 A | 12/1986 | Spector | |
| 5,023,020 A * | 6/1991 | Machida et al. | 261/18.1 |
| 5,071,621 A * | 12/1991 | Tokuhiro et al. | 422/4 |
| 5,078,046 A | 1/1992 | Mascolo et al. | |
| 5,102,189 A | 4/1992 | Saito et al. | |
| 5,297,988 A | 3/1994 | Nishino et al. | |
| 5,429,180 A | 7/1995 | Nishino et al. | |
| 5,724,256 A * | 3/1998 | Lee et al. | 700/285 |
| 6,357,726 B1 | 3/2002 | Watkins | |
| 6,494,778 B2 * | 12/2002 | Kossak et al. | 454/157 |
| 6,723,146 B2 | 4/2004 | Ninomiya et al. | |
| 6,834,847 B2 | 12/2004 | Bartsch et al. | |
| 7,097,555 B2 | 8/2006 | Bourbon | |
| 7,431,120 B2 | 10/2008 | Pollehn et al. | |
| 8,269,640 B2 * | 9/2012 | Ueno et al. | 340/632 |
| 2003/0034902 A1 * | 2/2003 | Dickau | 340/945 |
| 2005/0126841 A1 * | 6/2005 | Isaji et al. | 180/272 |
| 2005/0246100 A1 * | 11/2005 | Nath et al. | 701/301 |
| 2006/0113687 A1 | 6/2006 | Castellano | |
| 2007/0023540 A1 | 2/2007 | Selander | |
| 2007/0041865 A1 | 2/2007 | Ayoub et al. | |
| 2007/0138660 A1 | 6/2007 | Guo | |
| 2008/0111687 A1 | 5/2008 | Husmann | |
| 2008/0188172 A1 * | 8/2008 | Hollemans et al. | 454/75 |
| 2008/0207107 A1 * | 8/2008 | Matsuo et al. | 454/152 |
| 2008/0267833 A1 | 10/2008 | Manne | |
| 2008/0299014 A1 | 12/2008 | Kim | |
| 2009/0104072 A1 | 4/2009 | Ando et al. | |

FOREIGN PATENT DOCUMENTS

| | | |
|---|---|---|
| DE | 10305480 A1 | 8/2004 |
| JP | 2002283844 A | 10/2002 |
| WO | WO 0015269 A1 * | 3/2000 |
| WO | 2004044861 A1 | 5/2004 |
| WO | WO 2008117757 A1 * | 10/2008 |

* cited by examiner

*Primary Examiner* — Joseph Rocca
*Assistant Examiner* — Robert A Coker
(74) *Attorney, Agent, or Firm* — Vichit Chea; Price Heneveld LLP

(57) ABSTRACT

An in-vehicle smell notification system including a vehicle operating computer. A detector is operably connected with the vehicle operating computer and adapted to identify multiple external stimuli. A scent emitter includes multiple scent reservoirs. A controller is operably connected with the detector and the scent emitter and adapted to identify each of the multiple external stimuli and release a predetermined scent from the scent emitter upon identification of a predetermined stimulus.

17 Claims, 2 Drawing Sheets

IN-VEHICLE SMELL NOTIFICATION SYSTEM

FIELD OF THE INVENTION

The present invention generally relates to an in-vehicle smell notification system.

BACKGROUND OF THE PRESENT INVENTION

Notification systems are used throughout a vehicle to relay information to a driver or a passenger. These systems typically do not relay the information in a manner recognizable by an individual's olfactory senses.

SUMMARY OF THE PRESENT INVENTION

One aspect of the present invention includes an in-vehicle smell notification system including a vehicle operating computer. A detector is operably connected with the vehicle operating computer and adapted to identify multiple external stimuli. A scent emitter includes multiple scent reservoirs. A controller is operably connected with the detector and the scent emitter and adapted to identify each of the multiple external stimuli and release a predetermined scent from the scent emitter upon identification of a predetermined stimulus.

Another aspect of the present invention includes an in-vehicle smell notification system including a detector disposed in a vehicle and adapted to identify multiple external stimuli. A scent emitter includes multiple scent reservoirs. A controller is operably connected with the detector and the scent emitter and adapted to identify each of the multiple external stimuli and release a predetermined scent from the scent emitter upon identification of predetermined stimuli.

Yet another aspect of the present invention includes a method of relaying information to a passenger in a vehicle including providing a scent dispersion system having a detector operably connected with a controller. The controller is operably connected with a scent emitter. A predetermined stimulus is detected. A signal is sent from the controller to the scent emitter. Scent is released from the scent emitter.

These and other aspects, objects, and features of the present invention will be understood and appreciated by those skilled in the art upon studying the following specification, claims, and appended drawings.

BRIEF DESCRIPTION OF THE DRAWINGS

FIG. 3 is an interior perspective view of various components of one embodiment of an in-vehicle smell notification system; and FIG. 4 is a top plan view of a vehicle incorporating one embodiment of an in-vehicle smell notification system.

DETAILED DESCRIPTION OF THE PREFERRED EMBODIMENTS

Figure 1:
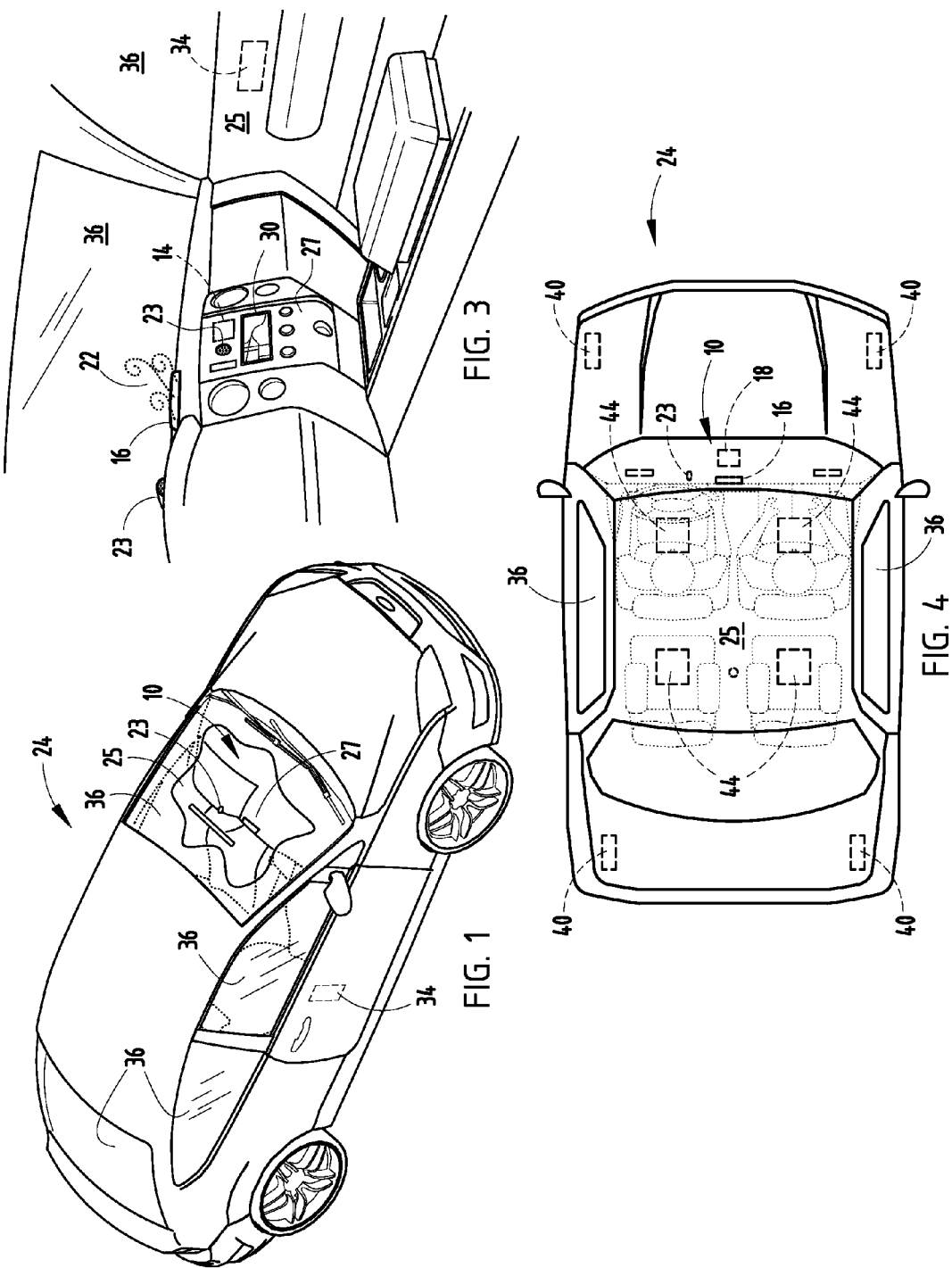
FIG. 1 is a top perspective view of one embodiment of a vehicle incorporating an in-vehicle smell notification system.

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Referring to FIGS. 1-4, the reference numeral 10 generally designates an in-vehicle smell notification system including a vehicle operating computer 12. A detector 14 is operably connected with the vehicle operating computer 12 and adapted to identify multiple external stimuli 15. A scent emitter 16 includes multiple scent reservoirs 18. A controller 20 is operably connected with the detector 14 and the scent emitter 16 and adapted to identify each of the multiple external stimuli 15 and release a predetermined scent 22 from the scent emitter 16 upon identification of one of the multiple external stimuli 15.

Referring to the embodiment illustrated in FIG. 1, the in-vehicle smell notification system 10 is located in a vehicle 24 and includes a voice recognition device 23 that is operably coupled with the detector 14 and accessible from an interior cabin 25 of the vehicle 24. The voice recognition device 23 is designed to recognize voice commands given by a driver or passenger in the vehicle 24. The voice recognition device 23 may also be operably connected with other systems in the vehicle 24.

Referring again to FIG. 1, the scent reservoirs 18 of the scent emitter 16 include multiple replaceable cartridges that include varying scents 22. The scents 22 may be formed of a gel, solid, or infused into an absorbable medium. Other possible constructions are also contemplated, as would be understood by a person having ordinary skill in the art.

The controller 20 is operably connected to a vehicle safety system. The vehicle safety system relays information to the controller 20 that pertains to accidents, damage to the vehicle 24, and system maintenance of the vehicle 24, among other information. For example, in the event the vehicle 24 is in an accident and rolls over, the vehicle safety system notifies the controller 20 that an accident has occurred. Consequently, the controller 20 requests verbal confirmation that the driver is safe and unharmed. In the absence of a verbal confirmation from the driver, the controller 20 sends a signal to the scent emitter 16 to expel a stimulation scent 22 from a smelling salt reservoir, thereby assisting in stimulating consciousness in the driver or passengers. In another embodiment, the controller 20 seeks a voice command from the driver or passenger, indicating that expulsion of a smelling salt is desired. After receiving the instructions, the in-vehicle smell notification system 10 would expel the smelling salt scent 22.

Figure 2:
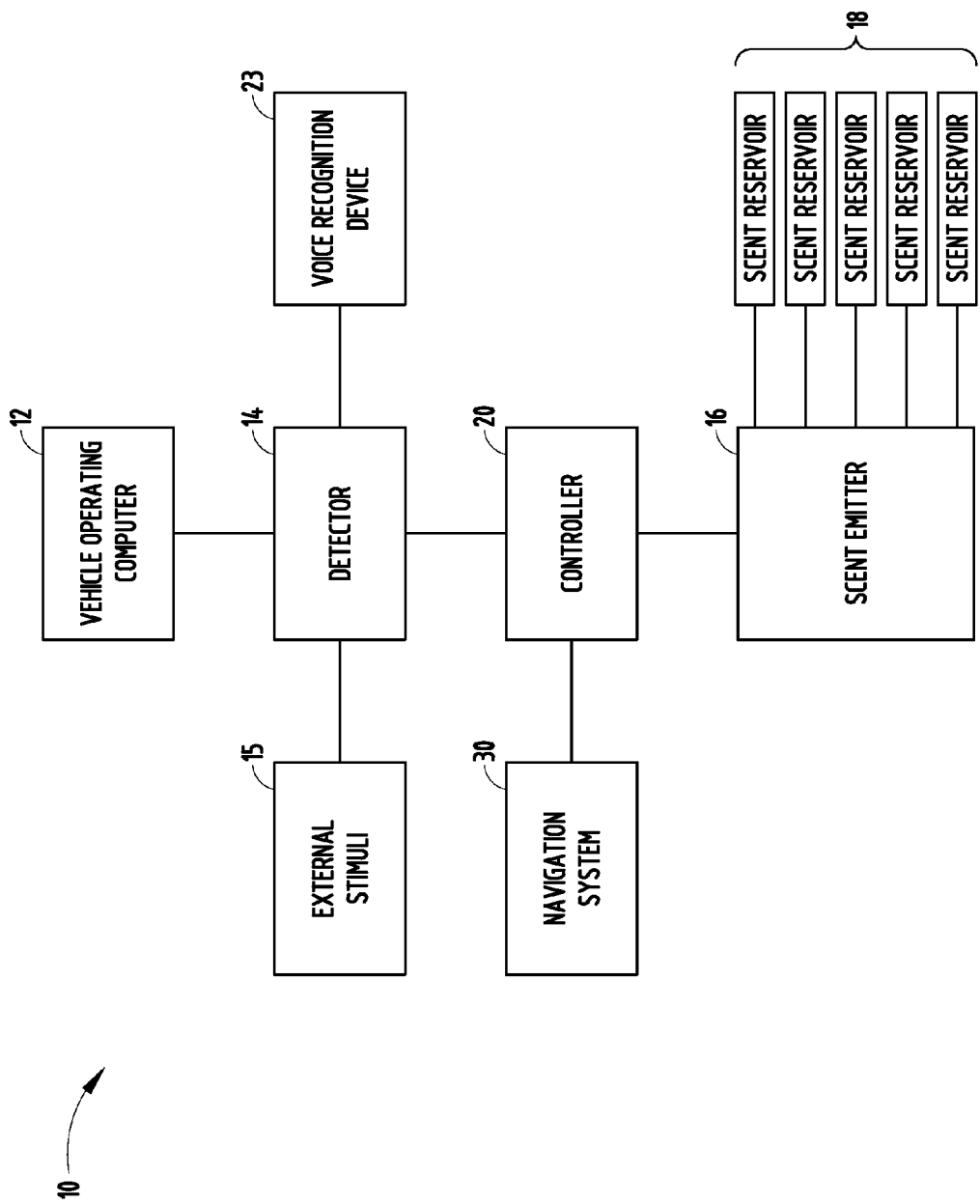
FIG. 2 is a flow chart of one embodiment of an in-vehicle smell notification system.

Referring now to the flow diagram illustrated in FIG. 2, the in-vehicle smell notification system 10 operates using the vehicle operating computer 12. The detector 14 is linked to the vehicle operating computer 12 and is designed to identify external stimuli 15. The external stimuli 15 can be internal or external sensors, the voice recognition device 23, or other possible stimuli. The controller 20 is operably connected with the detector 14, and may also be connected to the navigation system 30. The scent emitter 16, with the plurality of scent reservoirs 18, is connected to the controller 20 and designed to select a preferred scent reservoir 18 to emit scent after receiving a signal from the controller 20, which has consequently received a signal from the navigation system 30 or detector 14 that a preferred scent 22 should be emitted.

In yet another embodiment, if the vehicle 24 detects that a driver is drowsy or losing consciousness, based on the in-vehicle smell notification system 10, such as jerking of the steering wheel, then a coffee or a smelling salt scent 22 can be introduced into the cabin 25 of the vehicle 24.

Referring to the embodiment illustrated in FIG. 3, it is also contemplated that the controller 20 may be operably connected to a vehicle navigation system 30. Specifically, the controller 20 would receive instructions from the vehicle navigation system 30, and operate to modify the scent of the air when passing odorous sites that are recognized by the navigation system 30, such as wastewater treatment plants, tanneries, etc. In addition, in another embodiment, the in-vehicle smell notification system 10 is set up to disperse a particular scent 22 when the vehicle 24 enters a particular geographic area. As an example, the in-vehicle smell notification system 10 receives a notification that the vehicle 24 is within two miles of the driver's home. The in-vehicle smell notification system 10 then sends a signal to the scent emitter 16 to expel a particular scent 22 characterized as a "home scent."

As discussed above, it is contemplated that the controller 20 may also be connected to the vehicle operation system 27. The vehicle operation system 27 would relay information to the controller 20 concerning the operation of the vehicle 24. In the event that the vehicle operation system 27 notifies the driver of a potential system failure, for example, the vehicle 24 is low in oil, the controller 20 would then send a signal to the scent emitter 16 to expel a particular scent, such as an oil smell, indicating that the user needs to add oil to the vehicle 24.

In another embodiment, if the vehicle 24 is stolen, a strong and unpleasant odor, such as hydrogen sulfide or ammonia, may be released from a particular scent reservoir 18 in the scent emitter 16. Accordingly, the smell would deter a thief from driving a long distance in the vehicle 24. It is also contemplated that the vehicle operation system 27 may send a signal to windows motors 34 to deactivate, such that windows 36 on the vehicle 24 cannot be lowered to release the scent 22 from the cabin 25 of the vehicle 24.

As shown in the embodiment illustrated in FIG. 4, in another embodiment, the detectors 14 are multiple external sensors 40 disposed around the vehicle 24. The external sensors 40 are designed to release fragrances based on a positive or negative action that has occurred. For example, in the event the vehicle 24 is washed, the controller 20 would send a signal to the scent emitter 16 to release a cleaning product scent 22, thereby providing a new car smell. As another example, the vehicle 24 may have external sensors 40 that are sensitive to particular odors, and when the external sensors 40 detect a foul odor, the external sensors 40 send a signal to the controller 20 to activate the scent emitter 16 and emit a particular predetermined scent 22 into the cabin 25 of the vehicle 24.

In another embodiment, a masking agent scent 22 is expelled by the scent emitter 16. Specifically, the in-vehicle smell notification system 10 is notified, through voice commands, that an internal scent, such as flatulence of the driver or passenger, or an external smell, such as skunk, toxic smells, manure, etc., are present. The controller 20 then sends a signal to the scent emitter 16 to expel a pleasant or preferred scent 22, such as vanilla, apple, etc.

In yet another embodiment, the scent emitter 16 of the in-vehicle smell notification system 10 includes scent reservoirs 18 with therapeutic or medicinal materials disposed therein that can be expelled by the scent emitter 16 into the cabin 25 of the vehicle 24. As an example, one of the scent reservoirs 18 may include an asthmatic treating formula designed to assist the driver or passenger to breathe during an asthmatic episode. As another example, one of the scent reservoirs 18 may contain a material including camphor, eucalyptus oil, and methose, which are useful in suppressing coughs and treating sinus congestion.

Referring now to FIG. 4, in another embodiment, an occupant classification system or a seat memory setting can be used to identify particular occupants and/or drivers. In one embodiment, the detectors 14 are weight sensors 44, which detect a particular weight associated with a predetermined occupant. The weight sensors 44 send a signal to the controller 20, which sends a signal to the scent emitter 16 to release a predetermined scent 22. Once identified, a predetermined set of fragrant scents can be released into the cabin 25 of the vehicle 24. The predetermined set of fragrant scents would be based on preferred settings originally set by the occupant or driver. In addition, it is contemplated that the fragrance release could be linked to a timer linked with the controller 20. The timer can be set like a clock to send a signal to the controller 20, which in turn expels a predetermined scent 22 based on the time of day. More specifically, in the morning, for example, the driver could smell coffee, and in the evening, a comforting tea. In cold weather, a temperature sensor may send information that it is cold, snowy, or rainy, and release smells associated with the driver's favorite tea, hot chocolate, etc.

It is to be understood that variations and modifications can be made on the aforementioned structure without departing from the concepts of the present invention, and further it is to be understood that such concepts are intended to be covered by the following claims unless these claims by their language expressly state otherwise.

What is claimed is:

1. An in-vehicle smell notification system comprising:
 a vehicle operating computer;
 a detector operably connected with the vehicle operating computer and adapted to identify multiple external stimuli;
 a scent emitter having multiple scent reservoirs; and
 a controller operably connected with the vehicle operating computer and the detector and the scent emitter and adapted to release a predetermined scent from the scent emitter upon identification of a predetermined stimulus by the detector.

2. The in-vehicle smell notification system of claim 1, further comprising:
 a voice recognition device operably coupled with the detector.

3. The in-vehicle smell notification system of claim 1, wherein the scent reservoirs of the scent emitter include replaceable cartridges.

4. The in-vehicle smell notification system of claim 1, wherein the controller is operably connected to a vehicle safety system.

5. The in-vehicle smell notification system of claim 1, wherein the controller is operably connected to a vehicle navigation system.

6. An in-vehicle smell notification system comprising:
 a detector disposed in a vehicle and adapted to identify multiple external stimuli;
 a scent emitter having multiple scent reservoirs; and
 a controller operably connected with the detector and the scent emitter and adapted to identify each of the multiple external stimuli and release a predetermined scent from the scent emitter upon identification of a predetermined stimulus.

7. The in-vehicle smell notification system of claim 6, further comprising:
 a voice recognition device operably coupled with the detector.

8. The in-vehicle smell notification system of claim 6, wherein the scent reservoirs of the scent emitter include replaceable cartridges.

9. The in-vehicle smell notification system of claim 6, wherein the controller is operably connected to a vehicle safety system.

10. The in-vehicle smell notification system of claim 6, wherein the controller is operably connected to a vehicle navigation system.

11. A method of relaying information to a passenger in a vehicle comprising:
 providing a scent dispersion system having a detector operably connected with a controller;
 operably connecting the controller with a scent emitter;
 detecting a predetermined stimulus;
 sending a signal from the controller to the scent emitter;
 releasing scent from the scent emitter; and
 detecting voice commands given by a passenger in the vehicle.

12. The method of claim 11, wherein the step of detecting a predetermined stimulus further comprises:
 detecting an engine problem.

13. The method of claim 11, wherein the step of detecting a predetermined stimulus further comprises:
 detecting theft of the vehicle.

14. The method of claim 11, wherein the step of detecting a predetermined stimulus further comprises:
 detecting that the passenger is losing consciousness.

15. The method of claim 11, wherein the step of detecting a predetermined stimulus further comprises:
 detecting that the vehicle has been in an accident.

16. The method of claim 11, wherein the step of detecting a predetermined stimulus further comprises:
 detecting a seat memory setting which identifies a particular passenger.

17. The method of claim 11, wherein the step of detecting a predetermined stimulus further comprises:
 detecting a time of the day and releasing a predetermined scent associated therewith.

\* \* \* \* \*